United States Patent [19]

Wechsler et al.

[11] 4,370,272

[45] Jan. 25, 1983

[54] ALKOXYLATED QUATERNARY AMMONIUM SURFACTANTS

[75] Inventors: Joseph R. Wechsler, Chicago; Mark Lane, Shorewood, both of Ill.

[73] Assignee: Stepan Chemical Company, Northfield, Ill.

[21] Appl. No.: 301,402

[22] Filed: Sep. 11, 1981

Related U.S. Application Data

[63] Continuation-in-part of Ser. No. 111,688, Jan. 14, 1980, abandoned.

[51] Int. Cl.$^3$ ................................................ C11D 1/40
[52] U.S. Cl. .............................. 260/404; 260/501.13; 260/404.5; 252/9.8
[58] Field of Search ................ 260/50, 404, 404.5 Q, 260/501.13, 404.5 PA, 404.5 EO, 404.5 A

[56] References Cited

U.S. PATENT DOCUMENTS

| | | | |
|---|---|---|---|
| 3,833,597 | 9/1977 | Hardy et al. | 260/295 Q |
| 3,936,492 | 2/1976 | Samour et al. | 260/482 R |
| 3,954,845 | 5/1976 | Martinsson et al. | 260/501.13 |
| 4,038,294 | 7/1977 | Conner et al. | 260/404.5 |
| 4,118,525 | 10/1978 | Jones | 427/242 |
| 4,128,485 | 12/1978 | Bauman et al. | 260/404.5 |

*Primary Examiner*—Thomas A. Waltz
*Attorney, Agent, or Firm*—Hill, Van Santen, Steadman, Chiara & Simpson

[57] ABSTRACT

Esters of alkoxylated long chain fatty alcohols with halo acetic acid are contacted with tertiary amines incorporating a long chain aliphatic group to produce a class of novel quaternary ammonium compounds. These product compounds have utility as fabric softeners and as hair conditioners.

13 Claims, No Drawings

ALKOXYLATED QUATERNARY AMMONIUM SURFACTANTS

RELATED APPLICATION

This application is a continuation-in-part of my earlier U.S. patent application Ser. No. 111,688 filed Jan. 14, 1980, now abandoned, the entire disclosure and contents of which are incorporated hereinto by reference.

BACKGROUND OF THE INVENTION

Surfactants, it has heretofore been usual to make a surfactant for one particular end use application such as hair care or fabric softening. A class of compounds usable for hair care is not typically usable for fabric softening, and vice versa.

The art would like to use members of a given class of compounds having such utility for more than one end use application because this would reduce manufacturing investment capital and plant operating expenses. For example, it would be desirable to change compound structure within a given class only slightly and yet achieve a profound change in end use properties.

Conner et al U.S. Pat. No. 4,038,294 discloses fatty halo alkanoate quaternaries of dialkyl amino propyl amides to be useful for hair care applications only. No alkoxylated forms of these products are shown or suggested in Conner et al.

BRIEF SUMMARY OF THE INVENTION

This invention relates to a new and useful class of alkoxylated halo fatty alkanoate dimethyl amino quaternary derivatives which are useful as high molecular weight surfactants. Thus, for example, these derivatives can be used variously as hair care agents, fabric softening agents, coal dewatering agents, and the like, depending upon such variables as structure, formulation, and use conditions.

The presence of one or more alkoxy groups at one region in the molecule of these new compounds surprisingly and unexpectedly produces a profound effect upon one or more of these properties needed in specific end use applications. Thus, for example, in a fabric application, the presence of one alkoxy group profoundly affects the antistatic properties and to some extent the wicking properties; in hair care products, such alkoxy product affects the antistatic properties (which can be measured by the so-called fly-away procedure); and, in a coal dewatering application, the presence of alkloxy groups greatly enhance the wetting property of such a surfactant.

The new class of compounds provided by this invention is characterized by the formula:

$$\left[ \begin{array}{c} CH_3 \quad O \\ | \quad \quad \| \\ R^1-N-CH_2C-O-A_mR^2 \\ | \\ CH_3 \end{array} \right]^+ X^- \quad (1)$$

wherein $R^1$ is a radical selected from the group consisting of (a) straight chain aliphatic hydrocarbon radicals each of which contains from 12 through 24 carbon atoms, (b) ether radicals each of which has the structure: $R^3O(CH_2)_y-$, (C) amide radicals each of which has the structure

and (d) ester radicals each of which has the structure

$R^2$ is a straight chain aliphatic hydrocarbon radical containing from 12 through 32 carbon atoms, $R^3$ is a straight chain aliphatic hydrocarbon radical containing from 8 through 18 carbon atoms, $R^4$ is a straight chain aliphatic hydrocarbon radical containing from 7 through 17 carbon atoms, A is an alkoxy radical containing one oxygen atom and either two or three carbon atoms, X is an atom selected from the group consisting of bromine and chlorine, m is an integer of from 1 through 12, and y is an integer which is either 2 or 3.

This class of quaternary ammonium halide compounds inherently contains a substantial portion of fatty components which gives to such class of compounds a capacity to body fabric or hair to a desirable extent.

Also, this class of quaternary ammonium compounds readily exhausts substantively from aqueous solution or emulsion upon and into substrate surfaces, particularly such substrate surfaces as hair and fabric, as the case may be.

Still another feature of this invention is the circumstance that the quaternary ammonium halide compounds involved can be prepared from raw materials which are relatively inexpensive without adversely affecting the desired performance characteristics desired in fabric softening. Such raw materials are also characterized by having unusually long aliphatic chains which are now found to be surprisingly advantageous in such quaternary ammonium compounds for use in, for example, fabric softening, hair care, and coal dewatering.

Other and further objects, aspects, aims, purposes, features, advantages, and uses will be apparent to those skilled in the art from the present specification.

DETAILED DESCRIPTION

In one preparation procedure, to make a compound of formula (1) above, at least one halo lower alkanoate ester of a long chain fatty alcohol of the formula:

$$R^2A_mO-\overset{O}{\underset{\|}{C}}-CH_2X \quad (2)$$

wherein $R^2$, A, X, and m are as defined above, is contacted with a long chain aliphatic tertiary amine of the formula:

wherein $R^1$ is as defined above.

This contacting is conducted while maintaining the reaction system at a temperature of from about 60° to 90° C. for a time sufficient to substantially completely convert all the organic halide of formula (2), present into quaternary ammonium halide. About equimolar quantities of the tertiary amine of formula (3) and said fatty alcohol haloacetate of formula (2) are present at the start of such a contacting.

Compounds of formula (1) wherein m ranges from 1 to about 3 have utility as fabric softeners, and these compounds are characteristically not appreciably soluble in water. Compounds of formula (1) wherein m ranges from about 4 to 8 have utility as hair conditioning agents and these compounds are characteristically hydrophilic which tends to make them soluble in water. Compounds of formula (1) wherein m ranges from about 6 to about 12 have utility in reducing the amount of water retained on coal during coal dewatering.

Compounds of formula (2) are thus seen to be useful as intermediates in the manufacture of compounds of formula (1); formula (2) compounds, like compounds of formula (1), are believed to be novel.

Preferred compounds for fabric softening use of formula (1) are those wherein $R^1$ is an amide radical of the formula

(4)

wherein $R^4$ is alkyl radical containing from 15 through 17 carbon atoms, wherein $R^2$ is an alkyl radical containing from 12 through 32 carbon atoms, wherein A is an ethoxy radical, and wherein m is an integer of from 1 to 3 inclusive.

Preferred compounds for hair care use of formula (1) are those wherein $R^1$ is an amide radical of formula (4) above, wherein $R^4$ is an alkyl radical containing from 11 through 17 carbon atoms, wherein $R^2$ is an alkyl radical containing from 12 through 32 carbon atoms, wherein A is an ethoxy or propoxy radical, and wherein m is an integer of 4 to 8 inclusive.

Preferred compounds for coal dewatering use of formula (1) are those wherein $R^1$ is an aliphatic radical of formula (4) above, wherein $R^4$ is an alkyl radical containing from 15 through 17 carbon atoms, $R^2$ is an alkyl radical containing from 16 through 32 carbon atoms, wherein A is an ethoxy radical and wherein m is an integer of from 6 to 12 inclusive.

Compounds of formula (3) are known and can be prepared by a convenient synthetic technique. For example, when $R^1$ is the radical (a) as defined above in formula (1), then the tertiary amine of formula (3) is obtainable, for instance, by alkylating a fatty primary amine by the well known Leuckart reaction.

When $R^1$ is the radical (b) as defined in formula (1), then the tertiary amine of formula (3) is preparable by cyanoethylation of a fatty alcohol of proper chain length, followed by hydrogenation of the nitrile, followed by alkylation of the obtained primary amine to obtain a terminal tertiary amine group.

When $R^1$ is the radical (c) as defined in formula (1), then the amine of formula (3) can be prepared by reacting a fatty acid methyl ester with an amino (lower alkylene) dialkyl amine, such as illustrated by the following equation:

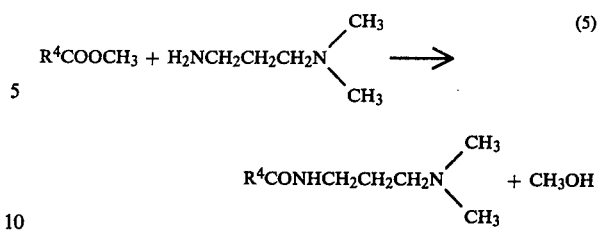
(5)

wherein $R^4$ is as defined above.

Another way to utilize an amide linkage for obtaining an amine compound of formula (3) is by a reaction between a fatty amine and an amino acid, such as follows:

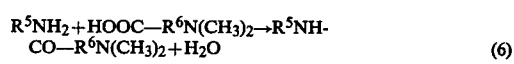
(6)

wherein $R^5$ is an alkyl radical containing from 12 through 18 carbon atoms, and $R^6$ is an alkylene radical containing either 1 or 2 carbon atoms.

When $R^1$ is the radical (d) as defined in formula (1) then the tertiary amine of formula (3) can be prepared by reacting a fatty acid methyl ester with a hydroxyl (lower alkylene) dialkyl amine, such as is illustrated by the following equations:

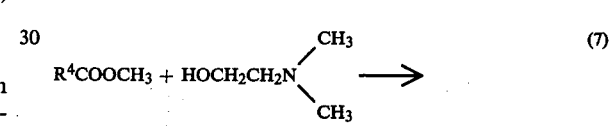
(7)

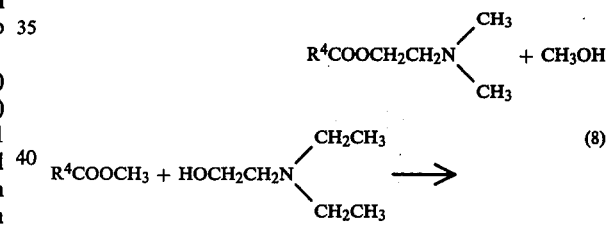
(8)

A salient feature of the method described in this invention for the preparation of products of formula (1) lies in the mildness of the reaction conditions. Such moderate conditions prevent charring and pyrolytic decomposition, thus protecting and enhancing the activity and the color of the final product. Moreover, it has been discovered that, unlike other nitrogen compounds, the compounds used in this invention, and even the intermediate esters used in making same, respond surprisingly well to bleaching with hydrogen peroxide, which makes it possible to obtain formula (1) products of remarkable lightness of color, if so desired.

For example, such intermediates of formula (2) can be bleached by using an amount of $H_2O_2$ ranging from 0.25 to 4.0 by weight percent (based on total ester) at a temperature of from about 70° to 80° C. under thorough agitation until no further lightening of color of the ester is obtained.

Bleaching of the quaternary is illustrated by certain examples below.

It is sometimes advantageous to use in the practice of this invention monohydric alcohols incorporating a very long straight chain aliphatic hydrocarbon radical which is mainly of the order of magnitude of about 20 to 32 carbon atoms per molecule. Such alcohols can be obtained, for instance, by the well known method named after K. Ziegler. In commerce, such alcohols are commercially available as byproducts usually containing from about 17 to 35% weight of an inert paraffin (total weight basis). If desired, the paraffins can be separated from the alcohols by a method described in this application.

Quaternary ammonium compounds obtained from such very high molecular weight alcohols, when prepared as a suitable product for use in fabric softening, display superior softening, wicking, and antistatic properties when compared with known commercial compounds currently in use for fabric softening, as shown, for example, by using testing methods which are known and accepted in the trade.

It is therefore possible, by using the synthetic methods disclosed herein, to manufacture the fabric conditioning compounds of formula (1) in superior quality and yet from low cost, raw materials.

When it is desired to prepare products of this invention for use in hair care, it is presently preferred to select molecules of formula (1) which tend to be soluble in water. Thus, a formula (1) compound is selected so as to impart sufficient hydrophilicity to a product to permit forming a clear solution thereof in water. Furthermore, when, in this application, it is desired to emphasize bodying, it is advantageous to select molecules in which either $R^1$ or $R^2$ of a formula (1) compound is a long chain alkyl group. Conversely, when it is desired in this application to emphasize absence of static electrical charge on the hair to be treated, it is now believed to be advantageous for $R^1$ and $R^2$ to be of relatively shorter chain lengths.

When it is desired to prepare products of this invention for use as fabric softeners, it is now believed to be advantageous to select molecules of formula (1) which tend to be water dispersable, but not water soluble. Therefore, for such application, m in formula (1) is preferably limited to a maximum of about 3.

The function of the alkoxy group in the case of hair care products of this invention is now believed not only to enhance water solubility, but also to promote a certain compatability of a cationic product of this invention, wherein m in formula (1) ranges from about 4 to 8, with anionic products of the prior art which are common ingredients of commercial shampoos. This particular feature is illustrated in Example 8 below.

Another way to utilize an ester linkage for obtaining a useful compound of formula (3) is by reacting a fatty alcohol with amino acid:

$$R^7(A)_zOH + HOOCR^6N(CH_3)_2 \rightarrow R^7(A)_zOCOR^6N(CH_3)_2 + H_2O \quad (9)$$

wherein $R^7$ is a straight chain alkyl radical containing from 16 to 32 carbon atoms, A is as defined above, and z is an integer of from (and including) 0 through 3, and $R^6$ is as defined above (in equation (6)).

Compounds of formula (2) are prepared, for example, by reacting a halo acetic acid of the formula:

$$XCH_2\overset{\overset{O}{\|}}{C}OH \quad (10)$$

wherein X is as above defined with a long chain fatty alcohol or a long chain polyalkoxylated alcohol of the formula:

$$HO(A)_mR^2 \quad (11)$$

where A, $R^2$ and m are as defined above.

This reaction is illustrated by the following equation:

$$C_{12}H_{25}O(CH_2CH_2O)_6H + HOOCCH_2Cl \longrightarrow \quad (12)$$

$$C_{12}H_{25}O(CH_2CH_2O)_6 - \overset{\overset{O}{\|}}{C}CH_2Cl + H_2O$$

The contacting of a formula (2) compound with a formula (3) compound is conveniently carried out at a temperature ranging from about 70° to 90° C. Preferably about equal respective molar quantities of formula (2) and formula (3) compounds are intermixed together before and during such contacting.

The function of the alkoxy group in the case of fabric softening products of this invention is now believed to be two-fold:
 (1) to produce fabric softeners which are self emulsifiable in water and thus need no added nonionic surfactant for obtaining stable emulsions; and
 (2) to produce fabric softeners of low melting range which need no added organic solvent.

Such alkylated fatty alcohols which are used in making the products of this invention can be manufactured in any convenient way; one such way is illustrated in Examples A–E hereunder.

In order to obtain enhanced bodying in either hair care or fabric softening application for compounds of this invention, it is desirable to use monohydric alcohols incorporating a very long straight chain aliphatic hydrocarbon radical containing from about 18 to 32 carbon atoms. Such alcohols can be obtained, for instance, by the well known method named after K. Ziegler. In commerce, such alcohols are commercially available as byproducts from the manufacture of alcohols of lower chain length, and such a byproduct usually contains also about 15 to 35% by weight of an inert paraffin. If desired, such inert paraffins can be separated from such byproduct alcohols by a method disclosed herein and illustrated in Example 3A hereunder.

The compounds of this invention can be readily formulated with aqueous systems for a hair care or a fabric conditioning application using the conventional techniques known to those skilled in the art.

EMBODIMENTS

The present invention is further illustrated by reference to the following Examples. Those skilled in the art will appreciate that other and further embodiments are obvious and within the spirit and scope of this invention from the teachings of these present examples taken with the accompanying specification.

The following Examples illustrate preparation of intermediate esters useful in making compounds of this invention.

EXAMPLE A

Preparation of an alkoxy-chloracetate ester of the formula: $R^2O(C_2H_4O)_4COCH_2Cl$, wherein the starting alcohol is a mixture of ethoxylated lauryl and myristyl alcohols. Thus, $R^2$ contains 12 through 14 carbon atoms per molecule. Thus, 194 g of a lauryl-myristyl alcohol mixture of commerce ("ALFOL" 1214GC available from Conoco Chemicals Division of Continental Oil Company) is placed into a pressure vessel together with 0.5 g powdered KOH. The vessel is purged with nitrogen and pressurized with ethylene oxide. The mixture is heated to 110°–120° C. under thorough agitation and the alkoxylation reaction is pursued until 176 g of ethylene oxide has been absorbed.

370 g of the obtained ethylene oxide adduct is esterified with 94.5 g monochloroacetic acid in presence of 50 ml toluene at reflux temperature until 18 ml water reaction has accumulated in a Dean-Stark trap and no more water is condensed, signalling the end of the esterification step. The acid content of the ester product is found to be 0.005 meq/g (milliequivalents per gram). The toluene is driven off by distillation under reduced pressure. There is obtained 446.5 g of chloroacetate ester. The color of this ester is considerably improved by bleaching with 1% $H_2O_2$ by weight of ester while holding reactants (the ester) at 70° to 75° C. for 1–2 hours.

EXAMPLE B

Preparation of an alkoxy-chloroacetate ester of the formula: $R^2O(C_2H_4O)_6COCH_2Cl$ wherein $R^2$ is a straight chain aliphatic hydrocarbon radical containing from 16 through 18 carbon atoms. Thus, the procedure of Example A is repeated with 258 g of a synthetic $C_{16}$-$C_{18}$ fatty alcohol available commercially as "EPAL 1618" from Ethyl Corporation Industrial Chemicals Division, (in place of the lauryl-myristyl alcohol of Example A) until 264 g ethylene oxide has been absorbed. 522 g of this ethylene oxide adduct is esterified and bleached in a manner described in Example A.

EXAMPLE C

Preparation of an alkoxy-chlooacetate ester of the formula:

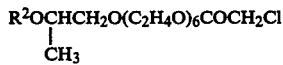

where $R^2$ is a straight chain alkyl radical containing from 18 through 32 carbon atoms per molecule. Thus, the procedure of Example A is repeated with 50 5 g of a synthetic monohydric alcohol mixture obtained commercially from Ethyl Corp. under the trade designation "EPAL 20+", reportedly having the following composition:

| | |
|---|---|
| $C_{18}$-$C_{32}$ primary alcohols: | 66.5% |
| $C_{24}$-$C_{40}$ paraffins: | 33.5% |

The composition of the alcohol portion reportedly is as follows:

| | |
|---|---|
| short than $C_{18}$: | 1% |
| $C_{18}$: | 6 |
| $C_{20}$: | 30 |
| $C_{22}$: | 19.5 |
| $C_{24}$: | 15 |
| $C_{26}$: | 12 |
| $C_{28}$: | 7.5 |
| $C_{30}$: | 4.5 |
| $C_{32}$: | 4.5 |

The alkoxylation step is carried out in two stages: First stage proceeds until 58 g propylene oxide has been absorbed, then second stage proceeds until 264 g ethylene oxide has been absorbed. Then, 827 g of the product ethoxylate is esterified and bleached in the manner described in Example A. There is obtained 903.5 g of an ester compound containing 81.3% chloroacetate acid ester and about 18.5% inert paraffins.

EXAMPLE D

Preparation of an alkoxy-chloroacetate ester of the formula: $R^2OC_2H_4OCOCH_2Cl$, where $R^2$ is a straight chain aliphatic hydrocarbon radical containing from 16 through 18 carbon atoms. Here, the process of Example B is repeated using 44 g of ethylene oxide. The alkoxylation step is allowed to proceed until all of the ethylene oxide has been absorbed. 302 g of the obtained adduct is esterified and bleached as described in Example A.

EXAMPLE E

Preparation of an alkoxy-chloroacetate ester of the formula: $R^2O(C_2H_4O)_2COCH_2Cl$ where $R^2$ is a straight chain aliphatic hydrocarbon radical containing from 18 through 32 carbon atoms per molecule. The process of Example C is repeated with the difference that the ethoxylation step is terminated when 88 g of ethylene oxide has been absorbed. 593 g of the adduct is esterified and bleached by the process of Example A. There is obtained 669.5 g of an ester product containing 74.7% chloracetate ester and 25.3% inert paraffins.

EXAMPLE F

Preparation of an amidoamine of the formula: $R^4CONHCH_2CH_2CH_2N(CH_3)_2$, wherein $R^4$ is a mixed aliphatic hydrocarbon radical derived from lauric and myristic acids. Thus 222 g of a mixture of the methyl esters of lauric and myristic acids (1 mole) obtained from coconut oil is mixed with 112 g (1.1 moles) dimethylamino-propylamine and 2.7 g (0.05 moles) $NaOCH_3$ under a nitrogen blanket at 90° to 95° C. Methanol is distilled as formed, and the reaction is driven to completion by applying reduced pressure (about 60 mm Hg) for about one hour at 95°–105° C. followed by ½ hour under 15–20 mm Hg pressure to remove the excess dimethylamino-propylamine. There is obtained 295 g of an ester compound containing about 96% amidoamine.

EXAMPLE G

Preparation of an amidoamine of the formula: $R^4CONHCH_2CH_2CH_2N(CH_3)_2$ where $R^4$ is an alkyl radical containing 17 carbon atoms. Thus, the process of Example F is repeated with 296 g methyl oleate. There is obtained 370 g of a product containing about 95% amidoamine.

EXAMPLE H

Preparation of an esteramine of the formula: $R^4COOCH_2CH_2N(CH_3)_2$, where $R^4$ is an alkyl radical containing 15 carbon atoms. Thus, 270 g (1 mole) methyl palmitate is mixed with 107 g (1.2 moles) dimethyl-ethanolamine in presence of 1.35 g (0.025 moles) NaOCH$_3$ under a nitrogen blanket at 90° C. while methanol is removed from the reaction zone by distillation. When the distillation slows down considerably after about 3 hours, the pressure is reduced to about 50 mm Hg to drive the reaction to completion, all the while keeping reactants at 95° C., and about one hour thereafter the pressure is further reduced to about 5 mm Hg to remove excess dimethylamino-ethanolamine. There is obtained 329 g of a viscous liquid containing about 97% amine-ester.

The following Examples illustrate the preparation of compounds of this invention.

EXAMPLE 1

Preparation of a quaternary ammonium chloride of the formula:

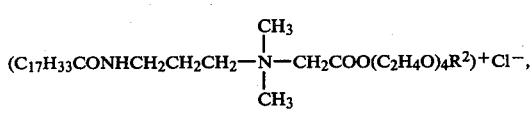

wherein the R$^2$ radical contains 12 through 14 carbon atoms. 447 g of an alkoxy ester of Example A is introduced into 385 g of an amidoamine of Example G at 75°–80° C. under a nitrogen blanket with thorough agitation over a period of about 45 minutes. The reaction mass is continuously stirred at 75°–80° C. in an inert atmosphere until the amine content, which is determined by HClO$_4$ titration, drops to below 0.01 meq/g and ionic chloride content reaches about 1.20 meq/g. The material so obtained is a viscous liquid soluble in water, containing about 97.5% quaternary ammonium chloride of molecular weight 812.5. The color of this material is improved considerably by bleaching with 1% H$_2$O$_2$ by weight of material at 75° C. for about 4 hours.

EXAMPLE 2

Preparation of a quaternary ammonium chloride of the formula:

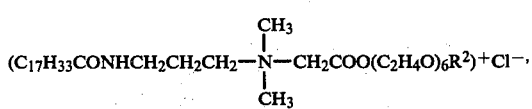

wherein the R$^2$ radical contains 16 through 18 carbon atoms. The process of Example 1 is repeated with 598.5 g ester of Example B replacing the ester of Example A. There is obtained 983.5 g of a light colored viscous liquid containing about 98% quaternary ammonium chloride of molecular weight 964.5. This material forms clear solutions in water.

EXAMPLE 3

Preparation of a quaternary ammonium chloride of the formula:

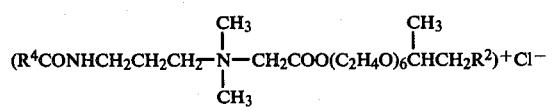

wherein the R$^4$ radical contains 11 through 13 carbon atoms and the R$^2$ radical contains 18 through 32 carbon atoms. The process of Example 1 is repeated with 903.5 g ester of Example C and 304 g amidoamine of Example F. There is obtained 1207.5 g of a viscous liquid containing about 85% quaternary ammonium chloride of molecular weight 1026.5 and 14% inert paraffins.

EXAMPLE 3a

Removal of paraffins from the product of Example 3: 1207.5 g product of Example 3 is dispersed in about 2400 g (twice its weight) of boiling methanol under thorough agitation for about 15 minutes, the mixture is cooled to room temperature, and the paraffin precipitates almost quantitatively together with part of the impurities (soap, etc.) contributed by the amidoamine of Example F. The precipitate is removed by filtration and the methanol is driven off the filtrate by vacuum distillation. There is obtained 1036 g of a light colored viscous liquid containing about 99% quaternary ammonium chloride of molecular weight 1026.5. This product forms clear solutions in water.

EXAMPLE 4

Preparation of a quaternary ammonium chloride of the formula:

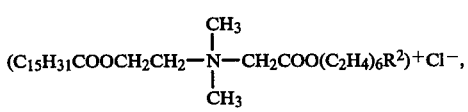

wherein the R$^2$ radical contains 16 through 18 carbon atoms. The process of Example 1 is repeated with 598.5 g of an ester of Example B and 337 g of an esteramine of Example H. There is obtained 935.5 g of a light colored viscous liquid containing about 99% quaternary ammonium chloride of molecular weight 925.5. This product forms clear solutions in water.

EXAMPLE 5

Preparation of a quaternary ammonium chloride of the formula:

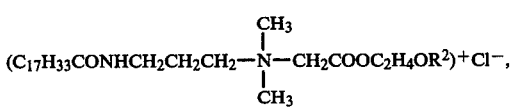

wherein the R$^2$ radical contains 16 through 18 carbon atoms. The process of Example 1 is repeated with 378.5 g of an ester of Example D replacing the ester of Example A. There is obtained 763.5 g of a pasty material of light color containing 97.5% quaternary ammonium chloride of molecular weight 744.5. For the sake of handling, this product is diluted with 63.5 g isopropanol. This material is not soluble in water, but it is easily dispersed in water forming stable emulsions.

EXAMPLE 6

Preparation of a quaternary ammonium chloride of the formula

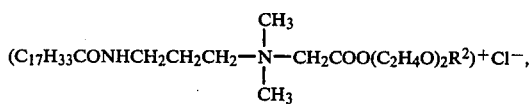

wherein the $R^2$ radical contains 18 through 32 carbon atoms. The process of Example 1 is repeated with 669.5 g of an ester of Example E replacing the ester of Example A. There is obtained 1054.5 g of a paste containing 82% quaternary ammonium chloride and 16% inert paraffins. This product is submitted to the purification procedure described in Example 3a wherein the paraffins are removed. There is obtained 878 g of a light colored paste containing 99% quaternary ammonium chloride of molecular weight 866.5. This product is diluted with 85 g isopropanol. The obtained 90% material is not soluble in water, but it is easily dispersed in water forming stable emulsions.

EXAMPLE 7

A 3% solution in distilled water of each of the compounds of Examples 1, 2, 3 and 4 is prepared. Samples of human hair swatches are immersed into the respective solutions and then dried. The hair treated by each of these solutions displays better surface properties (such as softness to the touch, compatability, and "fly-away") when compared to untreated hair.

EXAMPLE 8

A clear solution in water is prepared with the following ingredients:
 750 g sodium lauryl sulfate
 150 g lauric diethanol amide
 4000 g distilled water
This solution is divided into 5 equal parts of 980 g each. 20 g each of the compounds of Examples 1, 2, 3 and 4 are dissolved into parts 1, 2, 3 and 4, respectively, and 20 g water is added to part 5. Swatches of human hair are washed in each of these 5 solutions, rinsed with distilled water, and dried. The hair samples treated in the respective solutions 1 through 4 have surface properties superior to the hair treated in that solution above identified as part 5.

EXAMPLE 9

An 8% by weight aqueous emulsion of each of the compounds of Examples 5 and 6 is prepared by dispersing 89 g of each into 911 g water. The two emulsions so obtained are found to be stable for at least 3 months at room temperature. Washed and dried fabrics treated with either of the two emulsions by dispersing 45 g of each into 16 gallons of cold water used in the rinse cycle display superior surface properties, such as softness to the touch, wicking, and absence of static charge, when compared to fabrics not treated with a fabric softener like the compounds of Examples 5 and 6.

We claim:

1. A compound of the formula

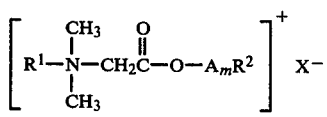

wherein
 $R^1$ is a radical selected from the group consisting of
 (a) straight chain aliphatic hydrocarbon radicals each of which contains from 12 through 24 carbon atoms, (b) ether radicals each of which has the structure: $R^3O(CH_2)_y-$, (c) amide radicals each of which has the structure

and (d) ester radicals each of which has the structure

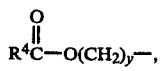

$R^2$ is a straight chain aliphatic hydrocarbon radical containing from 12 through 32 carbon atoms,
 $R^3$ is a straight chain aliphatic hydrocarbon radical containing from 8 through 18 carbon atoms,
 $R^4$ is a straight chain aliphatic hydrocarbon radical containing from 7 through 17 carbon atoms,
 A is an alkoxy radical containing one oxygen atom and either two or three carbon atoms,
 X is an atom selected from the group consisting of bromine and chlorine,
 m is an integer of from 1 through 12, and
 y is an integer which is either 2 or 3.

2. A compound of the formula

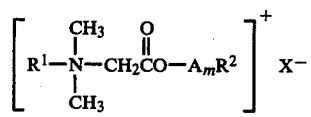

wherein
 $R^1$ is an amide having the structure

$R^2$ is a straight chain aliphatic hydrocarbon radical containing from 12 through 32 carbon atoms,
 $R^4$ is a straight chain aliphatic hydrocarbon radical containing from 7 through 17 carbon atoms,
 A is an alkoxy radical containing one oxygen atom and either two or three carbon atoms,
 X is selected from the group consisting of bromine and chlorine,
 m is an integer of from 1 through 12, and
 y is an integer which is either 2 or 3.

3. A compound of the formula

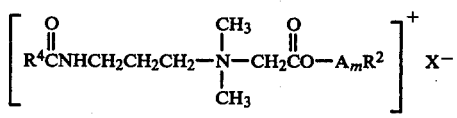

wherein
 $R^4$ is a straight chain aliphatic hydrocarbon radical containing from 11 through 17 carbon atoms,
 $R^2$ is a straight chain aliphatic hydrocarbon radical containing from about 12 through 32 carbon atoms,
 A is an alkoxyl radical containing one oxygen atom and either two or three carbon atoms, X is selected from the group consisting of bromine and chlorine, and m is an integer of from 1 through 12.

4. A compound of claim 3 wherein m is an integer of from 4 through 8.

5. A compound of claim 3 wherein $R^4$ is a straight chain aliphatic hydrocarbon radical containing from 15 through 17 carbon atoms, and m is an integer of from 1 through 3.

6. A compound of claim 5 wherein $R^2$ is a straight chain aliphatic hydrocarbon radical which contains from 12 through 18 carbon atoms.

7. A compound of the formula

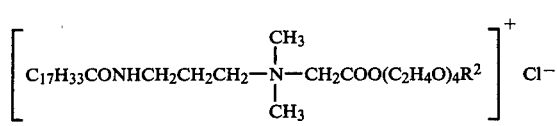

where $R^2$ is a straight chain aliphatic hydrocarbon radical containing from 12 through 14 carbon atoms per molecule.

8. A compound of the formula

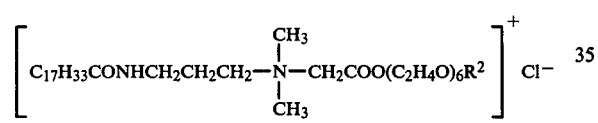

where $R^2$ is a straight chain aliphatic hydrocarbon radical containing from 16 through 18 carbon atoms per molecule.

9. A compound of the formula

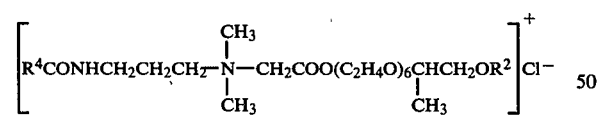

where $R^4$ is a straight chain aliphatic hydrocarbon radical containing from 11 through 13 carbon atoms, and $R^2$ is a straight chain aliphatic hydrocarbon radical containing from 18 through 32 carbon atoms.

10. A compound of the formula

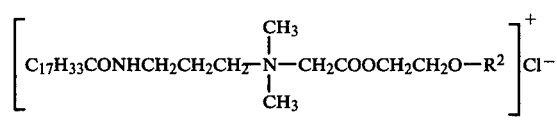

where $R^2$ is a straight chain aliphatic hydrocarbon radical containing from 18 through 32 carbon atoms per molecule.

11. A compound of the formula

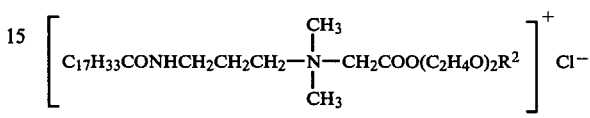

where $R^2$ is a straight chain aliphatic hydrocarbon radical containing from 18 through 32 carbon atoms per molecule.

12. A compound of the formula

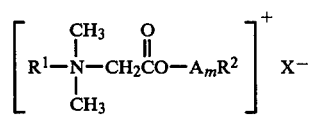

wherein $R^1$ is a radical having the structure

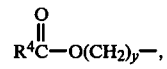

$R^2$ is a straight chain aliphatic hydrocarbon radical containing from about 12 through 32 carbon atoms, $R^4$ is a straight chain aliphatic hydrocarbon radical containing from 7 through 17 carbon atoms, A is an alkoxy radical containing one oxygen atom and either two or three carbon atoms, X is selected from the group consisting of bromine and chlorine, m is an integer of from 1 through 12, and y is an integer which is either 2 or 3.

13. A compound of the formula

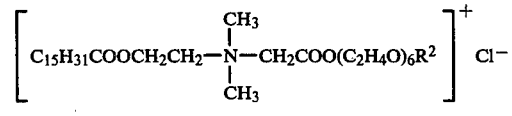

where $R^2$ is a straight chain aliphatic hydrocarbon radical containing from 16 through 18 carbon atoms per molecule.

* * * * *